(12) United States Patent
Payton et al.

(10) Patent No.: US 10,590,276 B2
(45) Date of Patent: Mar. 17, 2020

(54) AQUEOUS SUSPENSION OF INORGANIC PARTICULATE MATERIAL

(71) Applicant: ImerTech SAS, Paris (FR)

(72) Inventors: Desmond Charles Payton, Cornwall (GB); Stuart Thomas, London (GB)

(73) Assignee: ImerTech SAS, Paris (FR)

( * ) Notice: Subject to any disclaimer, the term of this patent is extended or adjusted under 35 U.S.C. 154(b) by 0 days.

(21) Appl. No.: 15/107,017

(22) PCT Filed: Dec. 19, 2014

(86) PCT No.: PCT/GB2014/053782
§ 371 (c)(1),
(2) Date: Jun. 21, 2016

(87) PCT Pub. No.: WO2015/097456
PCT Pub. Date: Jul. 2, 2015

(65) Prior Publication Data
US 2017/0088713 A1    Mar. 30, 2017

(30) Foreign Application Priority Data
Dec. 23, 2013 (GB) ................................ 1322840.8

(51) Int. Cl.
| C09D 7/00 | (2018.01) |
| C09C 1/02 | (2006.01) |
| C09C 3/08 | (2006.01) |
| A01N 33/08 | (2006.01) |
| C09K 15/20 | (2006.01) |

(52) U.S. Cl.
CPC .............. *C09C 1/021* (2013.01); *A01N 33/08* (2013.01); *C09C 3/08* (2013.01); *C09K 15/20* (2013.01); *C01P 2006/22* (2013.01)

(58) Field of Classification Search
None
See application file for complete search history.

(56) References Cited

U.S. PATENT DOCUMENTS

| 4,069,187 A | 1/1978 | Miller |
| 8,377,193 B2 | 2/2013 | Lortz et al. |
| 2006/0144290 A1 | 7/2006 | Polk et al. |
| 2010/0222484 A1 | 9/2010 | Buri et al. |
| 2011/0000397 A1* | 1/2011 | Lortz .................. B01F 17/0007 106/287.2 |

FOREIGN PATENT DOCUMENTS

| CN | 101348689 A | 1/2009 |
| CN | 102382496 A | 3/2012 |
| CN | 102702850 A | * 10/2012 | ............. C09D 11/10 |
| CN | 103396682 A | 11/2013 |
| EP | 1 860 164 A1 | 11/2007 |
| EP | 2 281 853 A1 | 2/2011 |
| EP | 2 329 712 A1 | 6/2011 |
| EP | 2 392 622 A1 | 12/2011 |
| JP | 09087116 A | 4/2009 |
| JP | 2009-523882 A | 6/2009 |
| JP | 2011-516646 A | 5/2011 |
| JP | 2011-122022 A | 6/2011 |
| WO | WO 2011/069961 A1 | 6/2011 |

OTHER PUBLICATIONS

CN 102702850 abstract (Year: 2012).*
International Search Report and Written Opinion dated Mar. 3, 2015, in International Application No. PCT/GB2014/063782 (10 pgs.).
GB Search Report dated Jun. 20, 2014, in GB Application No. GB1322840.8 (4 pgs.).
International Search Report and Written Opinion dated Mar. 10, 2015, in International Application No. PCT/GB2014/053782 (11 pgs.).
GB Search Report under Section 17 dated Jun. 19, 2014, in corresponding GB Application No. GB1322840.8 (2 pages).

* cited by examiner

*Primary Examiner* — Yun Qian
(74) *Attorney, Agent, or Firm* — Finnegan, Henderson, Farabow, Garrett & Dunner, LLP (57) ABSTRACT

An aqueous suspension comprising an inorganic particulate material and dimethylethanolamine, use of dimethylethanolamine to prevent pH decrease or reduce the rate of pH decrease of an aqueous suspension comprising an inorganic particulate material over time, use of dimethylethanolamine as an anti-microbial additive in an aqueous suspension comprising an inorganic particulate material, and a method of preparing an aqueous suspension comprising inorganic particulate material.

5 Claims, 3 Drawing Sheets

AQUEOUS SUSPENSION OF INORGANIC PARTICULATE MATERIAL

CLAIM FOR PRIORITY

This application is a U.S. national phase entry under 35 U.S.C. § 371 from PCT International Application No. PCT/GB2014/053782, filed Dec. 19, 2014, which claims the benefit of priority of GB Application No. 1322840.8, filed Dec. 23, 2013, the subject matter of both of which is incorporated herein by reference.

TECHNICAL FIELD

The present invention relates generally to an aqueous suspension comprising an inorganic particulate material and dimethylethanolamine. The present invention also relates to the use of dimethylethanolamine to prevent pH decrease or reduce the rate of pH decrease of an aqueous suspension comprising an inorganic particulate material over time. The present invention further relates to the use of dimethylethanolamine as an anti-microbial additive in an aqueous suspension comprising an inorganic particulate material. The present invention also relates to a method of preparing an aqueous suspension comprising an inorganic particulate material.

BACKGROUND OF THE INVENTION

The uses of inorganic particulate material are many and varied. Inorganic particulate material may, for example, be used as a filler or extender in numerous materials such as adhesives, sealants, glass, ceramics, rubber, paints, paper and plastics. The presence of an inorganic particulate material may provide advantageous properties such as colour, opacity, gloss, rheology, hardness, chemical resistance, thermal resistance or thermal conductivity. Calcium carbonate, for example, is often used in paints, plastics, film, adhesives and rubber.

Inorganic particulate materials are often stored and sold in aqueous suspensions. These aqueous suspensions may be stored for many days or weeks before they are used. The nature of the aqueous suspension may change over time, which may detrimentally affect the suitability of the aqueous suspension to be sold for an intended purpose.

For example, aqueous suspensions comprising an inorganic particulate material may be subject to pH change during storage.

For instance, the pH of an aqueous slurry of calcium carbonate generally decreases over time. Introduction of new calcium carbonate slurry product into a storage vessel over time may cause the pH of the calcium carbonate slurry to increase. Thus, the pH of the aqueous suspension may cycle during storage.

Without wishing to be bound by theory, it is believed that, in general, preparation of a calcium carbonate slurry forces carbon dioxide out of solution and produces an alkaline solution due to the presence of calcium and hydroxide ions. The calcium carbonate slurry may be stored in tanks for many days or weeks prior to delivery. During storage, the tanks may be stirred to prevent sedimentation and may also be recirculated (pumps circulate slurry from the bottom of the tank to the top). Drop in temperature of the slurry and exposure to air from stirring and recirculation contributes to atmospheric carbon dioxide dissolving back into the slurry. This causes the pH of the slurry to decrease (become more acidic) over time.

It is often important to maintain the pH of an aqueous suspension within a particular range so that it remains suitable for the purpose for which it is being sold. The pH of an aqueous suspension may also affect other properties of that aqueous suspension, which relate to the suitability of the aqueous suspension for its purpose. For example, the pH of a calcium carbonate slurry may affect its viscosity. At low pH values, the low shear slurry viscosity (Brookfield low shear) of the calcium carbonate slurry is higher.

It is thus desirable to prevent or reduce the rate of pH change of an aqueous suspension comprising an inorganic particulate material. For example, it is desirable to prevent pH decrease or reduce the rate of pH decrease of an aqueous suspension comprising inorganic particulate material over time. It may be beneficial to maintain the pH of an aqueous suspension within a particular pH range over a desired period of time.

Aqueous suspensions comprising inorganic particulate material may also be subject to contamination by microbes such as bacteria. This can negatively affect the properties of the aqueous suspension, for example by causing discolouration or malodour. It is thus desirable to prevent or limit the growth of microbes, or to reduce the number of microbes present in the aqueous suspension.

SUMMARY OF THE INVENTION

In accordance with a first aspect of the present invention, there is provided an aqueous suspension comprising an inorganic particulate material and dimethylethanolamine (DMEA).

In accordance with a second aspect of the present invention, there is provided a use of dimethylethanolamine (DMEA) to prevent pH decrease or reduce the rate of pH decrease of an aqueous suspension comprising inorganic particulate material over time.

In accordance with a third aspect of the present invention, there is provided a use of dimethylethanolamine (DMEA) as an anti-microbial additive in an aqueous suspension comprising inorganic particulate material.

In accordance with a fourth aspect of the present invention, there is provided a method of preparing an aqueous suspension of inorganic particulate material comprising combining water, inorganic particulate material and DMEA.

In certain embodiments of any aspect of the present invention, the inorganic particulate material is calcium carbonate, for example ground calcium carbonate.

In certain embodiments of any aspect of the present invention, the DMEA is present or used in an amount ranging from about 50 ppm to about 2000 ppm. In some embodiments, the DMEA may be present or used in an amount equal to about 600 ppm. In some embodiments, the DMEA may be present or used in an amount of less than about 600 ppm.

In certain embodiments of any aspect of the present invention, the aqueous suspension has a pH ranging from about 9.2 to about 10.5. In certain embodiments of any aspect of the present invention, the aqueous suspension has a pH ranging from greater than about 9.2 to about 10.5. In certain embodiments of any aspect of the present invention, the aqueous suspension has a pH ranging from about 9.2 to about 10.2, or from about 9.5 to about 10.5, or from about 9.5 to about 10.2.

In certain embodiments of any aspect of the present invention, the pH of the aqueous suspension is maintained in a pH range from about 9.2 to about 10.5 for an amount of time ranging from 1 day to 6 weeks. For example, the aqueous suspension may be maintained in a pH range from greater than about 9.2 to about 10.5, from about 9.2 to about 10.2, from about 9.5 to about 10.5, or from about 9.5 to about 10.2.

In certain embodiments of any aspect of the present invention, the pH of the aqueous suspension decreases by no more than 1 pH unit over 30 days.

In certain embodiments of any aspect of the present invention, the aqueous suspension has an initial viscosity ranging from about 100 to about 500 mPa·s.

In certain embodiments of any aspect of the present invention, the aqueous suspension is devoid of biocide. In alternative embodiments, the aqueous suspension further comprises biocide. In certain embodiments of the fourth aspect of the present invention, the method further comprises combining a biocide with the water, inorganic particulate material and DMEA.

In certain embodiments of any aspect of the present invention, the aqueous suspension is substantially devoid of microbes.

In certain embodiments of any aspect of the present invention, the aqueous suspension further comprises an additive which increases the pH of the aqueous suspension. In certain embodiments of the fourth aspect of the present invention, the method further comprises combining a further additive which increases the pH of the aqueous suspension, with the water, inorganic particulate material and DMEA. In certain embodiments, the additive is an amine. In certain embodiments, the additive is sodium hydroxide. The sodium hydroxide may be added in a blend with DMEA.

In particular embodiments of any aspect of the present invention, the aqueous suspension comprises calcium carbonate, for example ground calcium carbonate, and DMEA in an amount less than about 600 ppm.

In particular embodiments of any aspect of the present invention, the aqueous suspension comprises calcium carbonate, for example ground calcium carbonate, and has a pH ranging from about 9.2 to about 10.5.

In particular embodiments of any aspect of the present invention, the aqueous suspension comprises DMEA in an amount less than about 600 ppm and has a pH ranging from about 9.2 to about 10.5.

In particular embodiments of any aspect of the present invention, the aqueous suspension comprises calcium carbonate, for example ground calcium carbonate, DMEA in an amount less than about 600 ppm, and has a pH ranging from about 9.2 to about 10.5.

The details, examples and preferences provided in relation to any particular one or more of the stated aspects of the present invention apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION OF THE INVENTION

In certain embodiments of the present invention, an aqueous suspension comprising inorganic particulate material is provided which has advantageous properties, such as pH within a desired range and low levels of microbes. In other embodiments of the present invention, an improved process for controlling the pH and level of microbes in an aqueous suspension comprising inorganic particulate material is provided. In still other embodiments of the present invention, at least an alternative process of controlling the pH and level of microbes in an aqueous suspension comprising inorganic particulate material is provided.

In certain embodiments of the present invention, it was surprisingly found that dimethylethanolamine (DMEA) is able to prevent pH decrease or slow down the pH decrease of an aqueous suspension comprising an inorganic particulate material. In some embodiments of the present invention, it was surprisingly found that DMEA is able to at least prevent or reduce the rate of microbe growth, for example bacteria growth, in an aqueous suspension comprising an inorganic particulate material. In other embodiments of the present invention it was surprisingly found that DMEA is able to reduce the level of microbes, for example bacteria, in an aqueous suspension comprising an inorganic particulate material. In still other embodiments of the present invention, it was surprisingly found that DMEA works synergistically with biocides, thus improving the effectiveness of said biocides. This means that lower overall dose levels can be used to achieve a desired effect.

Aqueous Suspension

There is provided herein an aqueous suspension comprising, or consisting essentially of, or consisting of an inorganic particulate material and dimethylethanolamine (DMEA).

Inorganic Particulate Material

Any inorganic particulate material capable of being provided in an aqueous suspension may be used in certain embodiments of the present invention. Suitable inorganic particulate materials may be selected from one or more of the following: alkaline earth metal carbonate (for example dolomite, i.e. $CaMg(CO_3)_2$), metal sulphate (for example gypsum), metal silicate, metal oxide (for example iron oxide, chromia, antimony trioxide or silica), metal hydroxide, wollastonite, bauxite, talc (for example, French chalk), mica, zinc oxide (for example, zinc white or Chinese white), titanium dioxide (for example, anatase or rutile), zinc sulphide, calcium carbonate (for example precipitated calcium carbonate (PCC), ground calcium carbonate (GCC) or surface-modified calcium carbonate), barium sulphate (for example, barite, blanc fixe or process white), alumina hydrate (for example, alumina trihydrate, light alumina hydrate, lake white or transparent white), clay (for example kaolin, calcined kaolin, China clay or bentonite), and combinations thereof. The inorganic particulate material may be selected from any one or more of the materials listed. The inorganic particulate material may comprise a blend of any combination of the listed materials. Hereinafter, certain embodiments of the present invention may tend to be discussed in terms of calcium carbonate. However, the invention should not be construed as being limited to such embodiments.

When the inorganic particulate material used in certain embodiments of the present invention is obtained from naturally occurring sources, it may be that some mineral impurities will inevitably contaminate the ground material. For example, naturally occurring calcium carbonate occurs in association with other minerals. In general, however, the inorganic particulate material used in certain embodiments of the present invention will contain less than 5% by weight, preferably less than 1% by weight of other mineral impurities.

Calcium carbonate is particularly suitable for use in connection with certain embodiments of the present invention. Examples of calcium carbonate include ground calcium carbonate (GCC), precipitated calcium carbonate (PCC), dolomite and surface-modified calcium carbonate.

The particulate calcium carbonate used in certain embodiments of the present invention may be obtained from a natural source by grinding or may be prepared synthetically by precipitation (PCC), or may be a combination of the two, i.e. a mixture of the naturally derived ground material and the synthetic precipitated material. The PCC may also be ground.

Ground calcium carbonate (GCC) is typically obtained by grinding a mineral source such as chalk, marble or limestone, which may be followed by a particle size classification step, in order to obtain a product having the desired degree of fineness. The particulate solid material may be ground autogenously, i.e. by attrition between the particles of the solid material themselves, or alternatively, in the presence of a particulate grinding medium comprising particles of a different material from the calcium carbonate to be ground.

Wet grinding of calcium carbonate involves the formation of an aqueous suspension of the calcium carbonate which may then be ground, optionally in the presence of a suitable dispersing agent. Reference may be made to, for example, EP-A-614948 (the contents of which are incorporated by reference in their entirety) for more information regarding the wet grinding of calcium carbonate.

PCC may be used as the source of particulate calcium carbonate in certain embodiments of the present invention, and may be produced by any of the known methods available in the art. TAPPI Monograph Series No 30, "Paper Coating Pigments", pages 34-35 describes the three main commercial processes for preparing precipitated calcium carbonate which is suitable for use in preparing products for use in the paper industry, but may also be used in connection with the certain embodiments of the present invention. In all three processes, limestone is first calcined to produce quicklime, and the quicklime is then slaked in water to yield calcium hydroxide or milk of lime. In the first process, the milk of lime is directly carbonated with carbon dioxide gas. This process has the advantage that no by-product is formed, and it is relatively easy to control the properties and purity of the calcium carbonate product. In the second process, the milk of lime is contacted with soda ash to produce, by double decomposition, a precipitate of calcium carbonate and a solution of sodium hydroxide. The sodium hydroxide should be substantially completely separated from the calcium carbonate if this process is to be commercially attractive. In the third main commercial process, the milk of lime is first contacted with ammonium chloride to give a calcium chloride solution and ammonia gas. The calcium chloride solution is then contacted with soda ash to produce, by double decomposition, precipitated calcium carbonate and a solution of sodium chloride.

The process for making PCC results in very pure calcium carbonate crystals and water. The crystals can be produced in a variety of different shapes and sizes, depending on the specific reaction process that is used. The three main forms of PCC crystals are aragonite, rhombohedral and scalenohedral, all of which are suitable for use in certain embodiments of the present invention, including mixtures thereof.

The calcium carbonate, for example GCC or PCC, may optionally be surface-modified. The calcium carbonate may be coated. The coating may consist of, consist essentially of, or comprise a silane or any salt thereof, for example an organic silane. The calcium carbonate may be coated with a fatty acid or salt thereof. For example, the calcium carbonate may be coated with stearate.

The level of coating may be about 0.1 to about 10 wt % based on the total weight of the coated particulate mineral additive, for example between about 0.1 and about 3 wt %, for example between about 0.5 or 0.6 or 0.7 or 0.8 and about 2.0 wt % e.g. about 1.5 wt %.

The term "coating" used herein is to be understood broadly, and is not limited, for example, to uniform coatings or to coatings which cover the entire surface area of a particle. Particles in which discrete regions of the surface are modified with a coating will be understood as being coated within the terms of certain embodiments of the present invention.

The inorganic particulate material may be present in the aqueous suspension in an amount ranging from about 66 to about 82% by weight (solids content). For example, the inorganic particulate material may be present in the aqueous suspension in an amount ranging from about 70 to about 80% by weight, for example from about 74 to about 80% by weight, for example from about 74 to about 79% by weight. The solids content is the percentage mass of material remaining after the aqueous suspension has been dried to contain zero moisture. The solids content S is expressed as the percentage mass of the original material and is given by:

$$S = \frac{W3 - W1}{W2 - W1} \times 100$$

Where W1=the weight of sample dish;
W2=the weight of slurry plus sample dish; and
W3=the weight of dried material plus sample dish.

The inorganic particulate material(s) may have a $d_{10}$ from about 0.1 to about 0.5 μm.

The inorganic particulate material(s) may have a $d_{50}$ from about 0.6 to about 3 μm.

The inorganic particulate material(s) may have a $d_{90}$ from about 0.8 to about 10 μm.

Unless otherwise stated, particle size properties referred to herein for the particulate fillers or materials are as measured in a well known manner by sedimentation of the particulate filler or material in a fully dispersed condition in an aqueous medium using a Sedigraph 5100 machine as supplied by Micromeritics Instruments Corporation, Norcross, Ga., USA (telephone: +17706623620; web-site: www.micromeritics.com), referred to herein as a "Micromeritics Sedigraph 5100 unit". Such a machine provides measurements and a plot of the cumulative percentage by weight of particles having a size, referred to in the art as the 'equivalent spherical diameter' (e.s.d), less than given e.s.d values. The mean particle size $d_{50}$ is the value determined in this way of the particle e.s.d at which there are 50% by weight of the particles which have an equivalent spherical diameter less than that $d_{50}$ value. The $d_{98}$, $d_{90}$ and the $d_{10}$ are the values determined in this way of the particle e.s.d. at which there are 98%, 90% and 10% respectively by weight of the particles which have an equivalent spherical diameter less than that $d_{98}$, $d_{90}$ or $d_{10}$ value.

Dimethylethanolamine (DMEA)

Dimethylethanolamine (also known as N,N-dimethyl-2-aminoethanol, beta-dimethylaminoethyl alcohol, beta-hydroxyethyldimethylamine and Deanol) may be present in the aqueous suspension in an amount ranging from about 50 to about 2000 ppm. For example, DMEA may be present in the aqueous suspension in an amount ranging from about 50 ppm to about 1500 ppm, for example from about 50 ppm to about 1000 ppm, for example from about 50 ppm to about 800 ppm. DMEA may be present in the aqueous suspension in an amount ranging from about 100 to about 700 ppm, for example from about 200 to about 600 ppm, for example from about 200 to about 599 ppm, for example from about 300 to about 550 ppm.

DMEA may be present in the aqueous suspension in an amount equal to or less than about 700 ppm, for example DMEA may be present in the aqueous suspension in an amount less than 700 ppm. DMEA may be present in the aqueous suspension in an amount equal to or less than about 600 ppm, for example DMEA may be present in the aqueous suspension in an amount less than about 600 ppm. DMEA may be present in the aqueous suspension in an amount equal to or less than about 500 ppm, for example DMEA may be present in the aqueous suspension in an amount less than about 500 ppm.

Unless otherwise stated, the term "parts per million (ppm)" used herein, corresponds to mg of component (for example DMEA) per kg of dry weight of inorganic particulate material of the aqueous suspension.

pH

The pH of the aqueous suspension may, for example, range from about 9.2 to about 10.5 or from greater than about 9.2 to about 10.5. The pH of the aqueous suspension may, for example, range from about 9.2 to about 10.2, or from about 9.5 to about 10.5, or from about 9.5 to about 10.2. The pH of the aqueous suspension may, for example, range from about 9.3 to about 10.4, for example from about 9.4 to about 10.3 or from about 9.5 to about 10.2.

In certain embodiments, the pH of the aqueous suspension is maintained within the pH range from about 9.2 to about 10.5 for an amount of time ranging from 1 day to 6 weeks. The pH of the aqueous suspension may be maintained within the pH range from greater than about 9.2 to about 10.5 for an amount of time ranging from about 1 day to 6 weeks. The pH of the aqueous suspension may be maintained within the pH range from about 9.2 to about 10.2, or from about 9.5 to about 10.5, or from about 9.5 to about 10.2, for an amount of time ranging from 1 day to 6 weeks. The amount of time may range from about 1 week to about 6 weeks, or from about 2 weeks to about 6 weeks, or from about 3 weeks to about 6 weeks.

In certain embodiments, the pH of the aqueous suspension does not decrease by more than 1 pH unit over 30 days. For example, the pH of the aqueous suspension may not decrease by more than 0.8 pH units over 30 days, for example the pH of the aqueous suspension may not decrease by more than 0.5 pH units over 30 days.

The pH of the aqueous suspension may decrease by no more than 1 pH unit over 60 days, or may decrease by no more than 1 pH unit over 90 days, or may decrease by no more than 1 pH until over 120 days. For example, the pH of the aqueous suspension may decrease by no more than 0.8 pH units over 60 days, or 90 days or 120 days. For example, the pH of the aqueous suspension may decrease by no more than 0.5 pH units over 60 days, or 90 days, or 120 days.

The pH of the aqueous suspension may be measured using any conventional pH meter. For example, the pH of the aqueous suspension may be measured using the Digital pH meter "Mettler Toledo FE20", which has been calibrated in accordance with the manufacturer's instructions, using buffer solutions with nominal values of 4, 7 and 9. This may be carried out using either a manual or automatic method, depending on the type of instrument being used.

The pH of the aqueous suspension may be measured by:
mixing a sample of the aqueous suspension to ensure homogeneity, by using either the bench stirrer or the rotating rollers, or by shaking the sample container and contents vigorously;

measuring the temperature of the sample and adjusting the temperature to 22° C.;
removing the pH electrode from its deionised water storage solution and immersing it carefully into the test slurry;
waiting until a stable pH reading is obtained;
recording the pH value of the undisturbed slurry.

Viscosity

The initial viscosity of the aqueous suspension may range from about 100 to about 500 mPa·s. For example, the viscosity of the aqueous suspension may range from about 150 to about 450 mPa·s, or from about 200 to about 400 mPa·s, or from about 250 to about 350 mPa·s.

The initial viscosity of the aqueous suspension means the viscosity of the aqueous suspension immediately after preparation (viscosity measured at time 0). The viscosity of the aqueous suspension refers to the Brookfield low shear viscosity.

For example, measuring the viscosity of the aqueous suspension may comprise:
mixing a sample of the aqueous suspension to ensure that the slurry is homogeneous by using the bench stirrer or rotating rollers, or by shaking the container and contents vigorously;
measuring the temperature of the slurry and adjusting it to 22° C., either by cooling it in cold water or heating it in a water bath;
removing the sample from the water bath when the correct temperature is reached, and mixing the contents for approximately 3 minutes using a high speed bench stirrer, for example Hamilton Beach Model 936-IS, supplied by Hamilton Beach Scovill Inc. (Hamilton Beach Division), Washington, N.C., 2789, USA;
measuring viscosity by attaching a clean, dry number 3 spindle to a Brookfield RVT or Brookfield RVDE viscometer (supplied by Brookfield R. V. Viscometers: Brookfield Engineering Laboratories Inc., 240 Cushing Street, Stoughton, Mass. 02072, USA) and immersing it in the slurry to the groove. The spindle is centralised within the container containing the sample of aqueous suspension. The speed of the viscometer is set to 10 rotations per minute (r.p.m.) and switched on. The speed is increased to 100 r.p.m. and the spindle is allowed to rotate for 60 seconds±2 seconds. The viscometer reading is noted. The Brookfield RVT viscometer gives an analogue reading, whereas the Brookfield RVDE gives a digital reading.

If additional measurements of viscosity versus time are required, the lid is refitted to the container holding the sample and is returned to the water bath for the required time (tx). The viscosity is then measured and recorded as described above, after that time interval (tx). The sample should not be stirred or agitated prior to tx measurement.

Microbe Content

In certain embodiments, the aqueous suspension is substantially devoid of microbes. The term microbes may include one or more of the following: bacteria, viruses, archaea, protists, fungi, yeast.

In certain embodiments, the aqueous suspension is substantially devoid of bacteria. The aqueous suspension may be substantially devoid of one of more of the following bacteria: *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp.,

*Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. and mixtures thereof, and in certain embodiments is substantially devoid of bacteria selected from the group consisting of *Pseudomonas putida*, *Pseudomonas mendocina*, *Pseudomonas fluorescens*, *Pseudomonas alcaligenes*, *Pseudomonas pseudoalcaligenes*, *Pseudomonas entomophila*, *Pseudomonas syringae*, *Methylobacterium extorquens*, *Methylobacterium radiotolerants*, *Methylobacterium dichloromethanicum*, *Methylobacterium organophilu*, *Hyphomicrobium zavarzini* and mixtures thereof.

The aqueous suspension may be considered to be "substantially devoid" of microbes if it has a total viable count of less than about 1000 colony forming units (cfu) per millilitre, for example less than about 800 cfu/ml, for example less than about 500 cfu/ml, for example less than about 100 cfu/ml, for example less than about 10 cfu/ml. The aqueous suspension may be considered to be "substantially devoid" of microbes if it has a total viable count of 0 cfu/ml.

The total viable count of the aqueous suspension may range from about 0 cfu/ml to about 1,000,000 cfu/ml. For example, the total viable count of the aqueous suspension may range from about 10 cfu/ml to about 1,000,000 cfu/ml, for example from about 100 cfu/ml to about 500,000 cfu/ml, for example from about 100 cfu/ml to about 100,000 cfu/ml. The total viable count of the aqueous suspension may range from about 0 cfu/ml to about 1000 cfu/ml, for example from about 10 cfu/ml to about 1000 cfu/ml, for example from about 10 cfu/ml to about 100 cfu/ml.

The microbe level, for example the total viable count, of the aqueous suspension may be measured using growth medium such as Petrifilm or dipslides. The material under test (for example the aqueous suspension of inorganic particulate material) is diluted with a buffer solution and a measured amount of the dilution is placed on a growth medium (for example, Petrifilm). This is incubated for 48 hours, after which time the number of colonies of bacteria is counted. Each colony has developed from one single bacterium or colony forming unit (cfu). Therefore, the number of colonies, multiplied by the dilution factor, is equivalent to the number of original colony forming units per gram or millilitre of slurry.

For example, the total viable count of an aqueous suspension may be measured by:
mixing a sample of aqueous suspension of inorganic particulate material thoroughly by shaking its container vigorously;
measuring the required weight or volume of the sample. For example, if the results are to be recorded as colony forming units per g (cfu/g), a container containing the buffer solution is placed on the balance and the balance is set to zero. Approximately 1 g of slurry is weighed into the container and its weight is recorded to within 0.1 g. The contents of the container are mixed by shaking it vigorously. If the results are to be recorded as colony forming units per ml (cfu/ml), 1 ml of slurry may be added to a container containing the buffer solution. The contents of the container are mixed by shaking it vigorously;
distributing the diluted sample evenly on the growth medium. The plate may be left undisturbed for at least one minute to allow the gel to solidify;
incubating the contents of the growth medium (for example Petrifilm plates) for 48 hours±2 hours at 30° C.±2° C.;
counting the number of colonies on the growth medium (for example Petrifilm);
calculating the total viable count of the sample by multiplying the number of colonies on the growth medium (for example Petrifilm) by the dilution factor and dividing this by the weight or volume of the sample which was plated on the growth medium. For example:

$$\text{cfu/ml} = \frac{\text{number of colonies on growth medium} \times \text{dilution factor}}{\text{volume plated on growth medium}}$$

The total viable count of the aqueous suspension may be measured immediately after preparation (total viable count at time 0). The total viable count of the aqueous suspension may be measured 1 day after preparation, 3 days after preparation, 5 days after preparation or 7 days after preparation. The total viable count of the aqueous suspension may be measured up to 1 week after preparation, up to 2 weeks after preparation, up to 3 weeks after preparation, up to 4 weeks after preparation, up to 5 weeks after preparation or up to 6 weeks after preparation.

Biocide Content

The aqueous suspension may further comprise one or more biocides. The biocide(s) may be an aldehyde-releasing biocide, an aldehyde-based biocide, a phenolic biocide, an isothiazoline biocide, or any mixture thereof. The biocide may be selected from one or more of the following: formaldehyde, acetaldehyde, glyoxal, succinaldehyde, glutaraldehyde, 2-propenal, phthalic dialdehyde and mixtures thereof, and in certain embodiments is formaldehyde, glutaraldehyde, benzyl alcoholmono(poly)-hemiformal, ethyleneglycolhemiformal (EGHF), [1,2-Ethanediylbis(oxy)]-bis-methanol, tetrahydro-1, 3, 4, 6-tetrakis(hydroxylmethyl) imidazo [4,5-d]imidazole-2,5 (1H,3H)-dione (also commonly referred to as TetraMethylolAcetyleneDiurea TMAD), orthophenylphenol (OPP), 2-methyl-4-isothiazoline-3-one (MIT), 5-chloro-2-methyl-2H-isothiazolin-3-one (CIT), 1,2-benzisothiazoline-3-one (BIT), or mixtures thereof. The biocide may be a combination of 2-methyl-4-isothiazoline-3-one (MIT) and 1,2-benzisothiazoline-3-one (BIT).

The one or more biocide(s) may be present in the aqueous suspension in an amount ranging from about 50 ppm to about 2000 ppm, for example from about 50 ppm to about 1500 ppm, for example from about 50 ppm to about 1000 ppm. The one or more biocide(s) may be present in the aqueous suspension in an amount ranging from about 50 ppm to about 800 ppm, or from about 50 ppm to about 650 ppm, or from about 50 ppm to about 500 ppm or from about 50 ppm to about 400 ppm.

Alternatively, the aqueous suspension may be devoid of biocide.

Further Additives

The aqueous suspension may optionally further comprise other additives. For example, the aqueous suspension may further comprise one or more further optional additives which may have the effect of increasing the pH of the aqueous suspension, one or more dispersing agents, one or more thickening agents or one or more anti-settling agents.

The further optional additive may be selected from hydroxide-containing additives (for example alkali and alkali earth metal hydroxides, or for example sodium hydroxide, calcium hydroxide, potassium hydroxide, magnesium hydroxide, aluminium hydroxide or ammonium hydroxide), additives which generate hydroxide ions on reaction with water (for examples salts, such as sodium salts, of weak acids, for example sodium acetate, sodium bicarbonate, potassium carbonate and alkaline phosphates, for example sodium orthophosphate), and nitrogen-based additives (for example ammonia, amines and amides). The amine may be selected from primary, secondary or tertiary amines. The amine may be selected from monoethanolamine (MEA), diethanolamine (DEA), and methylaminoethanol (MAE). The further optional additive may be 2-amino-2-methyl-propanol (AMP).

The further optional additive may be added to the aqueous suspension sequentially with DMEA (for example a certain amount of pH increasing agent is added, followed by a certain amount of DMEA), or the further optional additive may be added to the aqueous suspension in a blend (in combination) with DMEA. The pH of the aqueous suspension may be higher when the further optional additive is added in a blend with DMEA in comparison to when the further optional additive is added sequentially with DMEA. For example, the further optional additive may be a hydroxide, for example sodium hydroxide, and the pH of the aqueous suspension of inorganic particulate matter may be higher when the hydroxide is added in a blend with DMEA in comparison to when the hydroxide is added sequentially with DMEA.

The dispersing agent may be made from monomers and/or co-monomers selected from the group consisting of acrylic acid, methacrylic acid, itaconic acid, crotonic acid, fumaric acid, maleic anhydride acid, isocrotonic acid, aconitic acid (cis or trans), mesaconic acid, sinapinic acid, undecylenic acid, angelic acid, canellic acid, hydroxyacrylic acid, acrolein, acrylamide, acrylonitrile, dimethylaminoethyl methacrylate, vinylpyrrolidone, vinylcaprolactam, ethylene, propylene, isobutylene, diisobutylene, vinyl acetate, styrene, [alpha]-methyl styrene, methyl vinyl ketone, the esters of acrylic and methacrylic acids and mixtures thereof. The dispersing agent may, for example, be polyacrylic acid and/or polymethacrlic acid.

The thickening agent may be selected from polyurethanes, acrylic polymers, latex, styrene, butadience, polyvinylalcohol, cellulose, cellulose-derived macromolecules, saccharides and organosilicones.

Use of DMEA to Prevent pH Decrease or Reduce the Rate of pH Decrease

Further provided herein is a use of DMEA to prevent pH decrease or reduce the rate of pH decrease of an aqueous suspension comprising an inorganic particulate material over time.

The pH of the aqueous suspension may, for example, range from about 9.2 to about 10.5, for example from greater than about 9.2 to about 10.5. The initial pH of the aqueous suspension may, for example, range from about 9.2 to about 10.2 or from about 9.5 to about 10.5 or from about 9.5 to about 10.2. The pH of the aqueous suspension may, for example, range from about 9.3 to about 10.4, for example from about 9.4 to about 10.3 or from about 9.5 to about 10.2.

The pH of the aqueous suspension may be measured immediately after preparation (pH at time 0). The pH of the aqueous suspension may be measured 1 day after preparation, 3 days after preparation or 5 days after preparation. The pH of the aqueous suspension may be measured up to 1 week after preparation, up to 2 weeks after preparation, up to 3 weeks after preparation, up to 4 weeks after preparation, up to 5 weeks after preparation or up to 6 weeks after preparation.

In certain embodiments, the pH of the aqueous suspension is maintained within the pH range from about 9.2 to about 10.5 for an amount of time ranging from 1 day to 6 weeks. The pH of the aqueous suspension may be maintained within the pH range from greater than about 9.2 to about 10.5 for an amount of time ranging from 1 day to 6 weeks. The pH of the aqueous suspension may be maintained within the pH range from about 9.2 to about 10.2, or from about 9.5 to about 10.5, or from about 9.5 to about 10.2 for an amount of time ranging from 1 day to 6 weeks. The amount of time may range from about 1 week to about 6 weeks, or from about 2 weeks to about 6 weeks, or from about 3 weeks to about 6 weeks.

In certain embodiments, the pH of the aqueous suspension does not decrease by more than 1 pH unit over 30 days. For example, the pH of the aqueous suspension may not decrease by more than 0.8 pH units over 30 days, for example the pH of the aqueous suspension may not decrease by more than 0.5 pH units over 30 days.

The pH of the aqueous suspension may decrease by no more than 1 pH unit over 60 days, or may decrease by no more than 1 pH unit over 90 days, or may decrease by no more than 1 pH until over 120 days. For example, the pH of the aqueous suspension may decrease by no more than 0.8 pH units over 60 days, or 90 days or 120 days. For example, the pH of the aqueous suspension may decrease by no more than 0.5 pH units over 60 days, or 90 days, or 120 days.

The pH of the aqueous suspension may be measured as described above in relation to the aqueous suspension.

The exact nature and composition of the aqueous suspension (including the amounts and type of inorganic particulate material and DMEA) may be as described above in relation to certain embodiments of the aqueous suspension described above.

Use of DMEA as an Anti-Microbial Additive

Further provided herein is a use of DMEA as an anti-microbial additive in an aqueous suspension comprising inorganic particulate material.

The term "anti-microbial" may mean that DMEA acts to prevent or inhibit the growth of microbes and/or that DMEA acts to reduce the rate of microbe growth and/or that DMEA acts to decrease the level of microbes (or total viable count) in an aqueous suspension.

In certain embodiments, DMEA is used as an anti-microbial additive such that the aqueous suspension is substantially devoid of microbes. The aqueous suspension may be considered to be "substantially devoid" of microbes if it has a total viable count of less than about 1000 colony forming units (cfu) per millilitre, for example less than about 800 cfu/ml, for example less than about 500 cfu/ml, for example less than about 100 cfu/ml, for example less than about 10 cfu/ml. The aqueous suspension may be considered to be "substantially devoid" of microbes if it has a total viable count of 0 cfu/ml.

The total viable count of the aqueous suspension may range from about 0 cfu/ml to about 1,000,000 cfu/ml. For example, the total viable count of the aqueous suspension may range from about 10 cfu/ml to about 1,000,000 cfu/ml, for example from about 100 cfu/ml to about 500,000 cfu/ml, for example from about 100 cfu/ml to about 100,000 cfu/ml. The total viable count of the aqueous suspension may range from about 0 cfu/ml to about 1000 cfu/ml, for example from about 10 cfu/ml to about 1000 cfu/ml, for example from about 10 cfu/ml to about 100 cfu/ml.

The microbe level, for example total viable count, of the aqueous suspension may be measured by the method described above.

The term microbes may include one or more of the following: bacteria, viruses, archaea, protists, fungi, yeast.

In certain embodiments, the aqueous suspension is substantially devoid of bacteria. The aqueous suspension may be substantially devoid of one of more of the following bacteria: *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. and mixtures thereof, and in certain embodiments is substantially devoid of bacteria selected from the group consisting of *Pseudomonas putida*, *Pseudomonas mendocina*, *Pseudomonas fluorescens*, *Pseudomonas alcaligenes*, *Pseudomonas pseudoalcaligenes*, *Pseudomonas entomophila*, *Pseudomonas syringae*, *Methylobacterium extorquens*, *Methylobacterium radiotolerants*, *Methylobacterium dichloromethanicum*, *Methylobacterium organophilu*, *Hyphomicrobium zavarzini* and mixtures thereof.

The aqueous suspension may further comprise one or more biocides. The biocide(s) may be an aldehyde-releasing biocide, an aldehyde-based biocide, a phenolic biocide, an isothiazoline biocide, or any mixture thereof. The biocide may be selected from one or more of the following: formaldehyde, acetaldehyde, glyoxal, succinaldehyde, glutaraldehyde, 2-propenal, phthalic dialdehyde and mixtures thereof, and in certain embodiments is formaldehyde, glutaraldehyde, benzyl alcoholmono(poly)-hemiformal, ethyleneglycolhemiformal (EGHF), [1,2-Ethanediylbis(oxy)]-bis-methanol, tetrahydro-1, 3, 4, 6-tetrakis(hydroxylmethyl) imidazo [4,5-d]imidazole-2,5 (1H,3H)-dione (also commonly referred to as TetraMethylolAcetyleneDiurea TMAD), orthophenylphenol (OPP), 2-methyl-4-isothiazoline-3-one (MIT), 5-chloro-2-methyl-2H-isothiazolin-3-one (CIT), 1,2-benzisothiazoline-3-one (BIT), or mixtures thereof. The biocide may be a combination of 2-methyl-4-isothiazoline-3-one (MIT) and 1,2-benzisothiazoline-3-one (BIT).

The one or more biocide(s) may be present in the aqueous suspension in an amount ranging from about 50 ppm to about 2000 ppm, for example from about 50 ppm to about 1500 ppm, for example from about 50 ppm to about 1000 ppm. The one or more biocide(s) may be present in the aqueous suspension in an amount ranging from about 50 ppm to about 800 ppm, or from about 50 ppm to about 650 ppm, or from about 50 ppm to about 500 ppm or from about 50 ppm to about 400 ppm.

When DMEA is used in combination with one or more biocide(s), the total microbe level (for example cfu/ml) of the aqueous suspension may be lower than that of an aqueous suspension that comprises the corresponding biocide(s), but does not comprise DMEA. The microbe level of the aqueous suspension comprising DMEA and one or more biocide(s) may decrease over time, for example over about 1 day or about 2 days or about 3 days or about 4 days or about 5 days or about 6 days or about 7 days. The microbe level of the aqueous suspension comprising DMEA and one or more biocide(s) may decrease at a faster rate than that of an aqueous suspension comprising the corresponding biocide(s) and in the absence of DMEA. The microbe level of the aqueous suspension comprising DMEA and one or more biocide(s) may decrease until the aqueous suspension is substantially devoid of microbes.

Alternatively, the aqueous suspension may be devoid of biocide.

When DMEA is used without biocide, the microbe level (for example cfu/ml) of the aqueous suspension may be lower than that of an aqueous suspension that does not comprise DMEA. The microbe level of the aqueous suspension comprising DMEA may decrease over time, for example over about 1 day or about 2 days or about 3 days or about 4 days or about 5 days or about 6 days or about 7 days. The microbe level of the aqueous suspension may decrease until the aqueous suspension is substantially devoid of microbes.

The use of DMEA (with or without an additional biocide) provides a lower microbe level at a lower dose in comparison to the same aqueous suspension with no DMEA addition.

The microbe level of the aqueous solution (for example total viable count) may be measured on the same day as introducing DMEA and the optional biocide(s), for example immediately after preparation. Alternatively or additionally, the microbe level may be measured 1 day, 2 days, 3 days, 4 days, 5 days, 6 days or 7 days after introducing DMEA and the optional biocide(s). Alternatively or additionally, the microbe level may be measured up to 2 weeks or 3 weeks or 4 weeks or 5 weeks or 6 weeks after introducing DMEA and the optional biocide(s).

The exact nature and composition of the aqueous suspension (including the amounts and type of inorganic particulate material and DMEA) may be as described above in relation to certain embodiments of the aqueous suspension described above.

Preparation Method

A method of preparing an aqueous suspension of inorganic particulate material is also provided herein. Said method comprises combining water, inorganic particulate material and DMEA.

The inorganic particulate material may be reduced in particle size using stirred media mills in the presence of commercially available synthetic media, water and commercially available organic dispersants such as sodium polyacrylate.

The inorganic particulate material may then be used to prepare aqueous suspensions comprising inorganic particulate material by any method known to those skilled in the art.

For example, the aqueous suspension may be prepared by adding 750 grams of dry coarse ground (<53 micron size) marble or limestone to a laboratory scale stirred media mill, along with 210 grams of deionised water. Commercially available sodium polyacrylate dispersant may be applied at a dose range of 0.22 to 0.35 of active sodium polacrylate per dry mineral weight. The contents may be stirred at high speed for a predetermined length of time to give a target wt %<2 micron cumulative particle size. The resultant mineral suspension may be separated from the media using screens.

The inorganic particulate material may be calcium carbonate, for example ground calcium carbonate (GCC).

DMEA may be used in an amount ranging from about 50 ppm to about 2000 ppm. For example, DMEA may be used in an amount ranging from about 50 ppm to about 1500 ppm, for example from about 50 ppm to about 1000 ppm, for example from about 50 ppm to about 800 ppm. The DMEA may be used in an amount ranging from about 100 to about 700 ppm, for example from about 200 to about 600 ppm, for example from about 200 to about 599 ppm, for example from about 300 to about 550 ppm.

DMEA may be present in the aqueous suspension in an amount equal to or less than about 700 ppm, for example DMEA may be present in the aqueous suspension in an amount less than 700 ppm. DMEA may be present in the aqueous suspension in an amount equal to or less than about 600 ppm, for example DMEA may be present in the aqueous suspension in an amount less than about 600 ppm. DMEA may be present in the aqueous suspension in an amount equal to or less than about 500 ppm, for example DMEA may be present in the aqueous suspension in an amount less than about 500 ppm.

The method may further comprise combining a biocide with the water, inorganic particulate material and DMEA. The biocide(s) may be an aldehyde-releasing biocide, an aldehyde-based biocide, a phenolic biocide, an isothiazoline biocide, or any mixture thereof. The biocide may be selected from one or more of the following: formaldehyde, acetaldehyde, glyoxal, succinaldehyde, glutaraldehyde, 2-propenal, phthalic dialdehyde and mixtures thereof, and in certain embodiments is formaldehyde, glutaraldehyde, benzyl alcoholmono(poly)-hemiformal, ethyleneglycolhemiformal (EGHF), [1,2-Ethanediylbis(oxy)]-bis-methanol, tetrahydro-1, 3, 4, 6-tetrakis(hydroxylmethyl)imidazo [4,5-d] imidazole-2,5 (1H,3H)-dione (also commonly referred to as TetraMethylolAcetyleneDiurea TMAD), orthophenylphenol (OPP), 2-methyl-4-isothiazoline-3-one (MIT), 5-chloro-2-methyl-2H-isothiazolin-3-one (CIT), 1,2-benzisothiazoline-3-one (BIT), or mixtures thereof. The biocide may be a combination of 2-methyl-4-isothiazoline-3-one (MIT) and 1,2-benzisothiazoline-3-one (BIT).

The one or more biocide(s) may be present in the aqueous suspension in an amount ranging from about 50 ppm to about 2000 ppm, for example from about 50 ppm to about 1500 ppm, for example from about 50 ppm to about 1000 ppm. The one or more biocide(s) may be present in the aqueous suspension in an amount raging from about 50 ppm to about 800 ppm, or from about 50 ppm to about 650 ppm, or from about 50 ppm to about 500 ppm or from about 50 ppm to about 400 ppm.

The exact nature and composition of the aqueous suspension (including the amounts and type of inorganic particulate material and DMEA) may be as described above in relation to certain embodiments of the aqueous suspension described above.

BRIEF DESCRIPTION OF THE DRAWINGS

Certain embodiments of the invention will now be described, by way of example only and without limitation with reference to the following Figures and Examples, in which.

EXAMPLES

Example 1

1 kg samples of a calcium carbonate slurry having 78 wt % solids and 60% of particles less than 2 μm in size (measured using a micrometrics sedigraph) were adjusted to pH at room temperature using 2-amino-2-methyl-1-propanol (AMP) or dimethylethanolamine (DMEA). The control sample was adjusted to pH 10 using dilute sodium hydroxide solution. The solids content of the samples was adjusted using deionised water.

The pH of each slurry was lowered to pH 8 by aspirating the sample with carbon dioxide ($CO_2$) enriched air (2%) using a flow rate of 5 mL/min. When pH 8 had been reached, aspiration of the sample was stopped.

Figure 1:
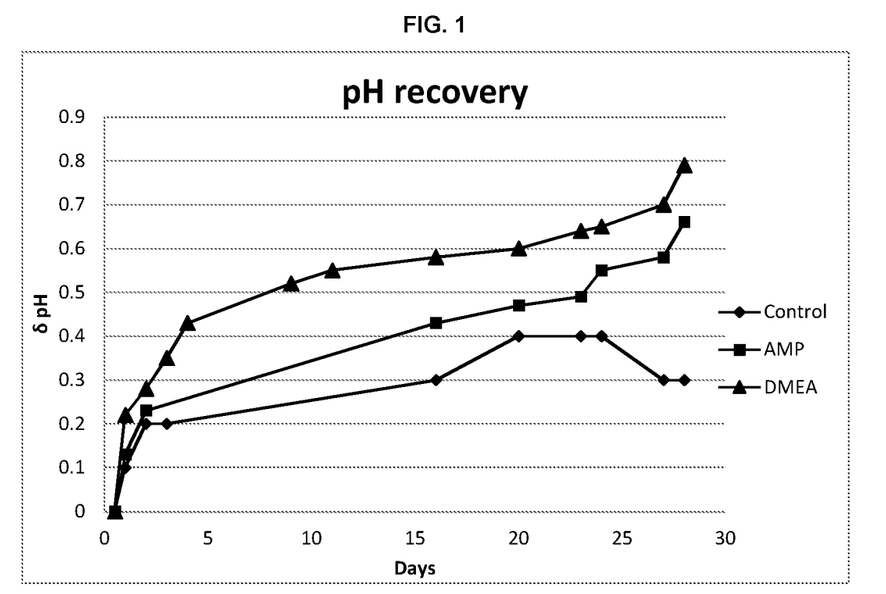
FIG. 1 shows the change in pH (δ pH) of the calcium carbonate slurry samples prepared in Example 1 over time.

Recovery of the sample pH was then monitored and recorded over subsequent days using the Mettler Toledo FE20 pH meter as described above in the detailed description. The results are shown in Table 1 and FIG. 1.

TABLE 1

| Day measurement taken | pH of Control sample | δ pH | pH of sample comprising AMP | δ pH | pH of sample comprising DMEA | δ pH |
|---|---|---|---|---|---|---|
| 0 | 9.20 | | 9.50 | | 10.00 | |
| 0.5 | 8.00 | 0.0 | 8.00 | 0.00 | 8.00 | 0.00 |
| 1 | 8.09 | 0.1 | 8.16 | 0.13 | 8.22 | 0.22 |
| 2 | 8.16 | 0.2 | 8.26 | 0.23 | 8.28 | 0.28 |
| 3 | 8.17 | 0.2 | | | 8.35 | 0.35 |
| 4 | | | | | 8.43 | 0.43 |
| 9 | | | | | 8.52 | 0.52 |
| 11 | | | | | 8.55 | 0.55 |
| 16 | 8.30 | 0.3 | 8.46 | 0.43 | 8.58 | 0.58 |
| 20 | 8.31 | 0.4 | 8.50 | 0.47 | 8.60 | 0.60 |
| 23 | 8.31 | 0.4 | 8.52 | 0.49 | 8.64 | 0.64 |
| 24 | 8.31 | 0.4 | 8.58 | 0.55 | 8.65 | 0.65 |
| 27 | 8.27 | 0.3 | 8.61 | 0.58 | 8.70 | 0.70 |
| 28 | 8.27 | 0.3 | 8.66 | 0.66 | 8.79 | 0.79 |

It was surprisingly found that the pH of the sample comprising DMEA increased to 8.8, whereas the pH of the control sample increased to 8.3. The pH of the sample comprising DMEA increased more rapidly and to a higher level than both the sample comprising AMP and the control sample.

In practice, the absorbed atmospheric carbon dioxide would not reduce the pH so dramatically and in such a rapid manner. As such, the addition of DMEA to an aqueous suspension would be more effective in maintaining slurry pH for a given period of time.

Example 2

Figure 2:
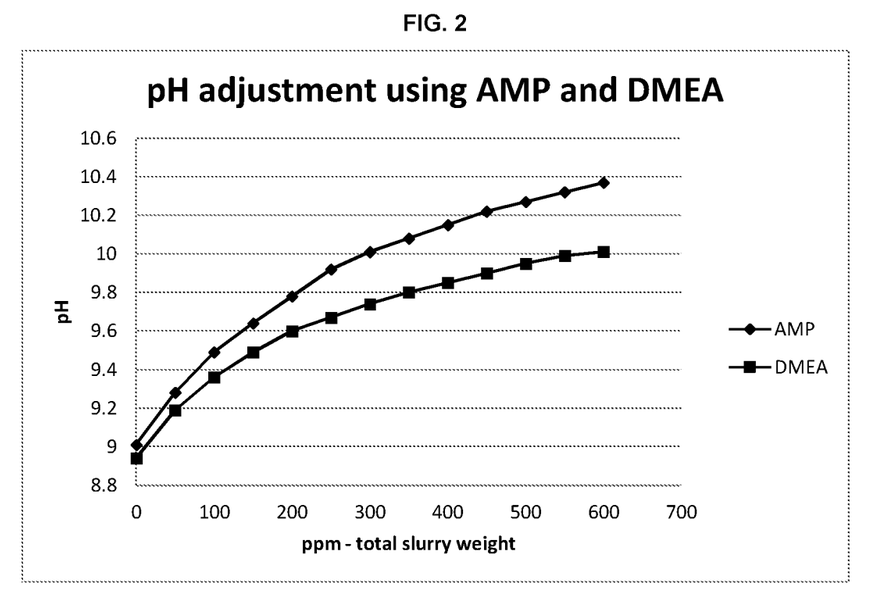
FIG. 2 shows the change in pH of calcium carbonate slurry samples as aliquots of 2-amino-2-methyl-1-propanol (AMP) or DMEA are added to the sample as described in Example 2.

50 mg/kg aliquots of either AMP or DMEA were sequentially added to 250 g calcium carbonate slurry samples having 78 wt % solids and 60% of particles less than 2 μm in size (measured using a micrometrics sedigraph). In this context, 50 mg/kg means that 50 mg of AMP or DMEA was added per kg of dry inorganic particulate material in the aqueous suspension. The pH of the samples was measured after stirring immediately after each 50 mg/kg addition. The results are shown in Table 2 and FIG. 2.

TABLE 2

| Total mg/kg of chemical added | Samples comprising AMP | | Samples comprising DMEA | |
| --- | --- | --- | --- | --- |
| | pH of sample | δ pH | pH of sample | δ pH |
| 0 | 9.01 | | 8.94 | |
| 50 | 9.28 | 0.27 | 9.19 | 0.25 |
| 100 | 9.49 | 0.21 | 9.36 | 0.17 |
| 150 | 9.64 | 0.15 | 9.49 | 0.13 |
| 200 | 9.78 | 0.14 | 9.60 | 0.11 |
| 250 | 9.92 | 0.14 | 9.67 | 0.07 |
| 300 | 10.01 | 0.09 | 9.74 | 0.07 |
| 350 | 10.08 | 0.07 | 9.80 | 0.06 |
| 400 | 10.15 | 0.07 | 9.85 | 0.05 |
| 450 | 10.22 | 0.07 | 9.90 | 0.05 |
| 500 | 10.27 | 0.05 | 9.95 | 0.05 |
| 550 | 10.32 | 0.05 | 9.99 | 0.04 |
| 600 | 10.37 | 0.05 | 10.01 | 0.02 |

The results show that a similar pH increase was seen with both AMP and DMEA.

Example 3

Figure 3:
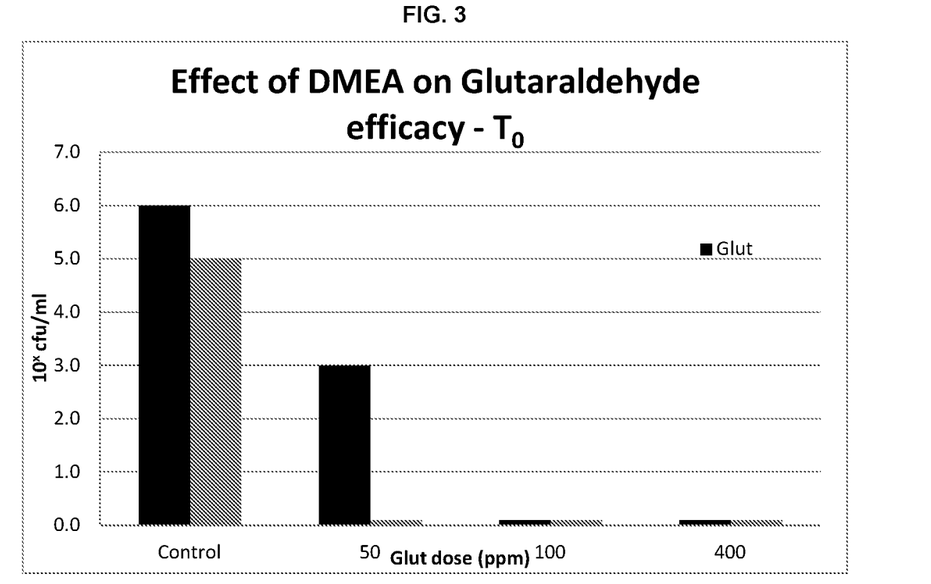
FIG. 3 shows the effect of increasing amounts of glutaraldehyde, both alone and in combination with 600 ppm of DMEA, on total viable count of the calcium carbonate slurry samples prepared in Example 3, after 0 days.

Samples of a contaminated calcium carbonate slurry having 78 wt % solids and 60% of particles less than 2 μm in size (measured using a micrometrics sedigraph) comprising various amounts of the biocide glutaraldehyde, and DMEA were prepared. The total viable count (cfu/ml) of each sample was measured after 0, 1 and 7 days by the method described above in the detailed description. The results are shown in Table 3 and FIG. 3.

TABLE 3

| | Chemical Addition (ppm) | | Total Viable Count (cfu/ml) of samples as $10^x$ | | |
| --- | --- | --- | --- | --- | --- |
| Sample | Glutar-aldehyde | DMEA | x(0 days after preparation) | x(1 day after preparation) | x(7 days after preparation) |
| 1 | 0 | 0 | 6 | 6 | 6 |
| 2 | 0 | 600 | 5 | 4 | 0.1 |
| 3 | 50 | 0 | 3 | 0.1 | 0.1 |
| 4 | 50 | 600 | 0.1 | 0.1 | 0.1 |
| 5 | 100 | 0 | 0.1 | 0.1 | 0.1 |
| 6 | 100 | 600 | 0.1 | 0.1 | 0.1 |
| 7 | 400 | 0 | 0.1 | 0.1 | 0.1 |
| 8 | 400 | 600 | 0.1 | 0.1 | 0.1 |

It was surprisingly found that samples comprising DMEA in combination with a 50 ppm dose of glutaraldehyde have a lower total viable count after 0 days in comparison with a sample comprising a 50 ppm dose of glutaraldehyde but no DMEA. The use of DMEA in combination with a 50, 100 or 400 ppm dose of glutaraldehyde is at least as effective in reducing total viable count after 1 and 7 days as using glutaraldehyde alone.

Example 4

Figure 4:
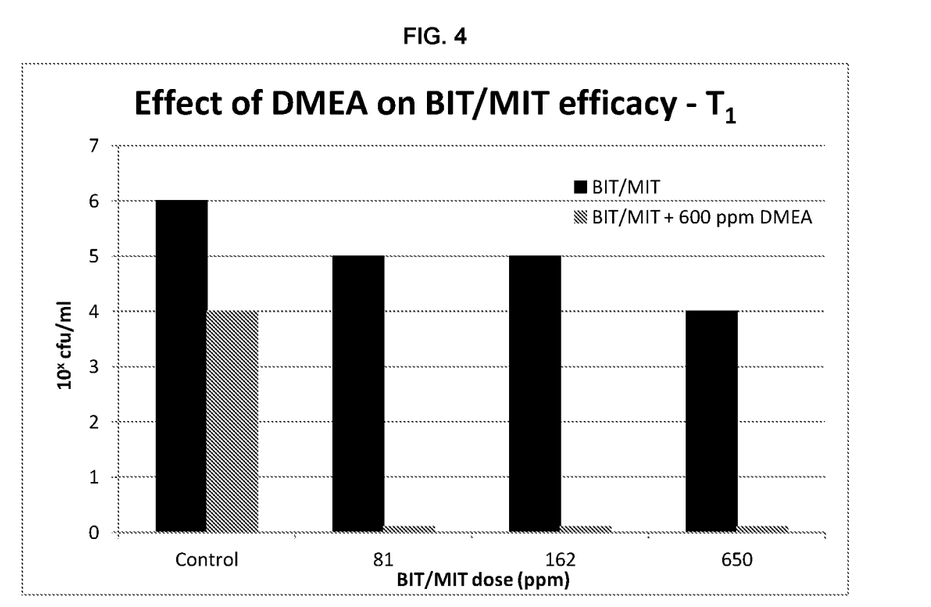
FIG. 4 shows the effect of increasing amounts of benzisothiazolinone and methylisothiazolinone, both alone and in combination with DMEA, on total viable count of the calcium carbonate slurry samples prepared in Example 4, after 1 day.

Samples of a contaminated calcium carbonate slurry having 78 wt % solids and 60% of particles less than 2 μm in size (measured using a micrometrics sedigraph) comprising various amounts of DMEA and the biocides benzisothiazolinone (BIT) and methylisothiazolinone (MIT) were prepared. The total viable count (cfu/ml) of each sample was measured after 0, 1 and 7 days by the method described above in the detailed description. The results are shown in Table 4 and FIG. 4.

TABLE 4

| | Chemical Addition (ppm) | | Total Viable Count (cfu/ml) of samples as $10^x$ | | |
| --- | --- | --- | --- | --- | --- |
| Sample | BIT/MIT | DMEA | x(0 days after preparation) | x(1 day after preparation) | x(7 days after preparation) |
| 1 | 0 | 0 | 6 | 6 | 6 |
| 2 | 0 | 600 | 5 | 4 | 0.1 |
| 3 | 81 | 0 | 5 | 5 | 4 |
| 4 | 81 | 600 | 5 | 0.1 | 0.1 |
| 5 | 162 | 0 | 5 | 5 | 4 |
| 6 | 162 | 600 | 5 | 0.1 | 0.1 |
| 7 | 650 | 0 | 5 | 4 | 0 |
| 8 | 650 | 600 | 4 | 0.1 | 0.1 |

It was surprisingly found that samples comprising DMEA in combination with a 81, 162 or 650 ppm dose of BIT/MIT had a lower total viable count after 1 day and 7 days than samples comprising BIT/MIT but no DMEA.

Example 5

Figure 5:
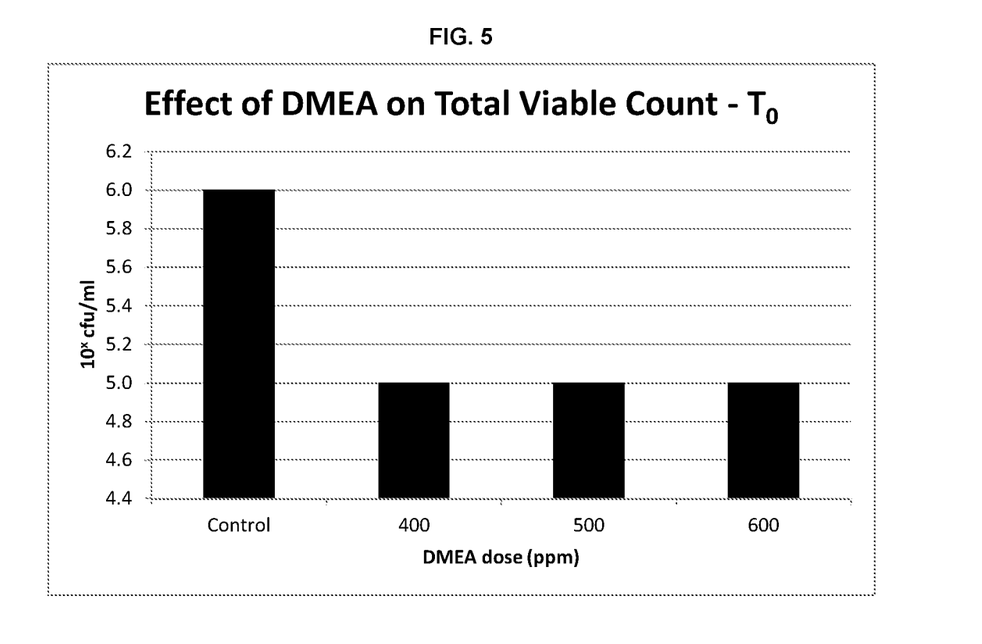
FIG. 5 shows the effect of increasing amounts of DMEA on total viable count of the calcium carbonate slurry samples prepared in Example 5, after 0 days.
Figure 6:
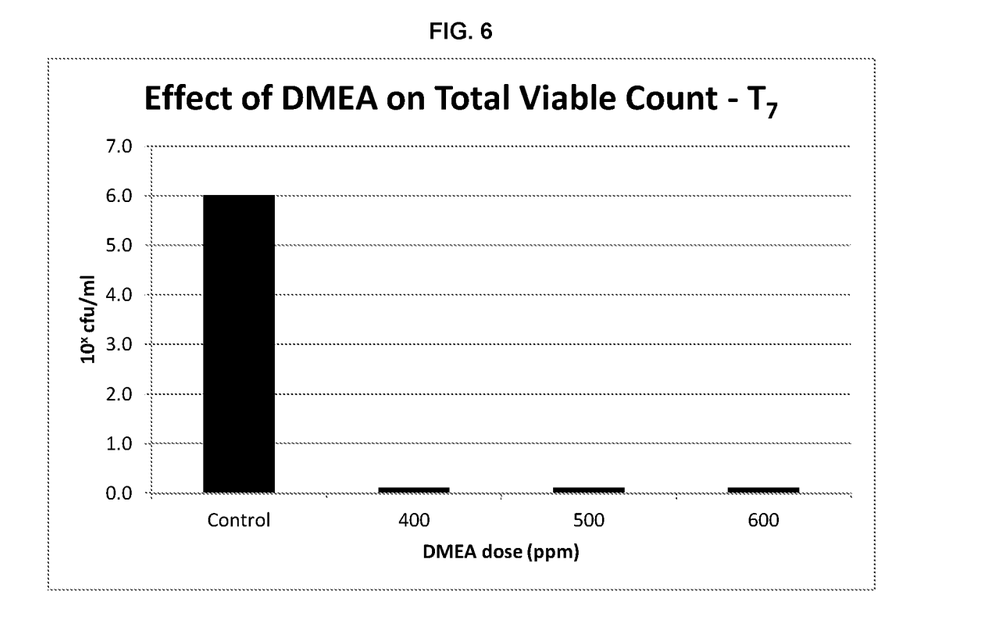
FIG. 6 shows the effect of increasing amounts of DMEA on total viable count of the calcium carbonate slurry samples prepared in Example 5, after 7 days.

Samples of a contaminated calcium carbonate slurry having 78 wt % solids and 60% of particles less than 2 μm in size (measured using a micrometrics sedigraph) comprising various amounts of DMEA were prepared. The total viable count (cfu/ml) of each sample was measured after 0, 1 and 7 days by the method described above in the detailed description. The results are shown in Table 5 and FIGS. 5 and 6.

TABLE 5

| | Total Viable Count (cfu/ml) of sample as $10^x$ | | |
| --- | --- | --- | --- |
| DMEA (ppm) in sample | x(0 days after preparation) | x(1 day after preparation) | x(7 days after preparation) |
| 0 | 6 | 6 | 6 |
| 400 | 5 | 4 | 0.1 |
| 500 | 5 | 4 | 0.1 |
| 600 | 5 | 4 | 0.1 |

It was surprisingly found that samples comprising 400, 500 and 600 ppm doses of DMEA alone (without any additional biocide) slightly reduced the level of microbes in the samples after 0 days, and further reduced the level of microbes in the samples after 1 day and 7 days in comparison with samples comprising no DMEA.

It was thus surprisingly shown that DMEA can be used as an anti-microbial additive in an aqueous suspension comprising inorganic particulate material, when used either alone or in combination with a biocide. DMEA can be used in a lower dose than other biocides to achieve the same microbe level (for example total viable count).

The foregoing broadly describes certain embodiments of the present invention without limitation. Variations and modifications as will be readily apparent to those skilled in the art are intended to be within the scope of the present invention as defined in and by the appended claims.

The invention claimed is:

1. A method comprising:
forming an aqueous suspension comprising an amount of 2-(Dimethylamino)ethanol (DMEA) and one of an alkaline earth metal carbonate, wollastonite, talc, or clay present in the aqueous suspension in an amount ranging from about 66% to about 82%, wherein
the pH of the aqueous suspension is maintained in a pH range from about 9.5 to about 10.5 for an amount of time ranging from 1 day to 6 weeks.

2. The method of claim 1, wherein the alkaline earth metal carbonate is calcium carbonate.

3. The method of claim 1, wherein the aqueous suspension has an initial viscosity ranging from about 100 to about 500 mPa·s.

4. The method of claim 1, wherein the aqueous suspension is devoid of biocide.

5. The method of claim 1, wherein the aqueous suspension further comprises an additive which increases the pH of the aqueous suspension.

\* \* \* \* \*